US005747078A

United States Patent [19]

De Jong et al.

[11] Patent Number: 5,747,078
[45] Date of Patent: May 5, 1998

[54] LONGTERM ANTIMICROBIAL ACTIVITY OBTAINED BY SUSTAINED RELEASE OF HYDROGEN PEROXIDE

[75] Inventors: Sylvia Josefine De Jong, Delft; Ben Rudolf De Haan, Voorburg; Hong Sheng Tan, Bleiswijk, all of Netherlands

[73] Assignee: Gist-brocades, N.V., Netherlands

[21] Appl. No.: 375,563

[22] Filed: Jan. 13, 1995

Related U.S. Application Data

[63] Continuation of Ser. No. 969,153, filed as PCT/NL92/00104, Jun. 11, 1992, abandoned.

[30] Foreign Application Priority Data

Jun. 11, 1991 [EP] European Pat. Off. ............ 91201442

[51] Int. Cl.$^6$ ................................................. A23C 19/00
[52] U.S. Cl. .................. 426/9; 426/10; 426/36; 426/330.2; 426/334; 426/580; 426/582; 435/175; 435/189; 435/190
[58] Field of Search ................................. 426/9, 10, 36, 426/38, 40, 42, 289, 310, 580, 582, 587, 330, 330.2, 334; 435/175, 177, 178, 179, 189, 190

[56] References Cited

U.S. PATENT DOCUMENTS

| 3,838,007 | 9/1974 | van Velzen | 435/96 |
|---|---|---|---|
| 4,320,116 | 3/1982 | Bjorck | 424/129 |
| 5,085,873 | 2/1992 | Degre | 426/8 |

FOREIGN PATENT DOCUMENTS

| 1167381 | 5/1984 | Canada. |
| 0397227 | 11/1990 | European Pat. Off.. |
| 0397228 | 11/1990 | European Pat. Off.. |
| 2153443 | 5/1973 | France. |
| 2237589 | 2/1975 | France. |
| 1468405 | 3/1977 | United Kingdom. |

OTHER PUBLICATIONS

Fennema, O. R., Food Chemistry, 1985, pp. 434–436. Marcel–Dekker, Inc., New York.

Schlech et al., "Epidemic Listeriosis–evidence for transmission by food" *New Engl. J. Med.* (1993) 308(4):203–206.

Fleming et al., "Pasteurized milk as a vehicle of infection in an outbreak of Listeriosis" *New Engl. J. Med.* (1985) 312(7):404–407.

Linnan et al., "Epidemic Listeriosis associated with mexican–style cheese" *New Engl. J. Med.* (1988) 319(13):823–828.

*Food Chem. News.* (Dec. 7, 1987) 29(40):17,32,41.

Reiter et al., "Lactoperoxidase antibacterial system: natural occurrence, biological functions and practical applications" *J. Food Protect.* (1984) 47(9):724–732.

Pruitt et al., eds., "Biochemistry of peroxidase system: antimicrobial effects" *The Lactoperoxidase System Chemistry and Biological Significance* (1985) Marcel Dekker, Inc., New York, New York, Chapter 8, pp. 143–178.

Hamid et al.; Multi–enzyme electrodes for the determination of starch by flow injection; *Chemical Abstracts*, 11324) (1990) Abstract No. 214158h.

*Primary Examiner*—Leslie Wong
*Attorney, Agent, or Firm*—Morrison & Foerster LLP

[57] ABSTRACT

Methods for long-term preservation of food products using a lactoperoxidase system. Long-term preservation is achieved by controlled generation of hydrogen peroxide as a substrate for the lactoperoxidase system. Controlled production of hydrogen peroxide is achieved by generating the hydrogen peroxide enzymatically form a system wherein the substrate for the enzyme generating the hydrogen peroxide is immobilized or is generated in situ from a precursor.

6 Claims, 19 Drawing Sheets

LONGTERM ANTIMICROBIAL ACTIVITY OBTAINED BY SUSTAINED RELEASE OF HYDROGEN PEROXIDE

This application is a continuation of application Ser. No. 07/969,153, filed Feb. 10, 1993 now abandoned, which is a 35 U.S.C. 371 national stage application of PCT/NL92/00104.

TECHNICAL FIELD

The present invention relates to an improvement in the se of an antimicrobial system. Specifically, the invention relates to the sustained release of hydrogen peroxide. The hydrogen peroxide produced may be used as such or it may be used in combination with suitable reactants to produce substances with antimicrobial activity, specifically hypothiocyanate.

BACKGROUND OF THE INVENTION

Microbial contamination of food and feed can cause severe health problems. Recent examples are the different outbreaks of human listeriosis that have been reported in Canada (Schlech et al. 1983. N.Engl.J.Med. 308 : 203–206), in the United States (Fleming et al. 1985. N.Engl.J.Med. 312: 404–407 and Linnan et al. 1988. N.Engl.J.Med. 319: 823–828) and in Switzerland (Food Chem. News. 1987. Dec, 7).

Microbial contamination can also adversely affect products containing proteins or other microbially degradable components.

Different methods to prevent microbial contamination of susceptible products are known such as, chemical methods (addition of compounds such as sulphite, nitrite, benzoic acid, sorbic acid) and the use of bacteriocins. Due to the suspected and proven side-effects of the chemicals used in the chemical methods, the acceptability of such methods is becoming more and more questionable. Furthermore, the applicability of bacteriocins is restricted due to the relatively high specificity of these molecules toward specific microorganisms. This would necessitate the use of mixtures of many different bacteriocins in order to be effective against microorganisms.

The disadvantages of the above-mentioned methods stimulated the search for more acceptable methods. One way to avoid the above problems is the use of naturally occurring antimicrobial systems. Turning the attention to natural mechanisms for preventing microbial growth, an antimicrobial system in milk was identified to be the so-called lactoperoxidase system (LP system). The use of this lactoperoxidase system, which has a broad range of applicability, is of increasing importance.

The lactoperoxidase/thiocyanate/hydrogen peroxide system is an antimicrobial system which is indigenous to the major body fluids such as raw milk, tears and saliva.

The properties of this system have been reviewed by Reiter and Harnülv (1984. J. Food Protect. 47: 724–732) and Pruitt and Reiter (1985. In 'The lactoperoxidase system chemistry and biological significance' Eds. Pruitt, K. M. and Tenovuo, D. p. 144–178 New York, Marcel Dekker, Inc.).

Schematically, the lactoperoxidase system can be represented by a three-step process;

a) the hydrogen peroxide production step; the reaction of an oxidoreductase with an oxidizable substrate with the concommitant production of hydrogen peroxide, b) the lactoperoxidase reaction step; in this step thiocyanate is converted to hypothiocyanate by reaction with hydrogen peroxide which reaction is catalyzed by lactoperoxidase, c) the antimicrobial reaction; wherein hypothiocyanate inactivates the microorganisms.

Instead of in situ production of the hydrogen peroxide, hydrogen peroxide can also be slowly added to the mixture to be protected. Furthermore, it is possible to use soluble inorganic peroxides from which peroxide is gradually released. For practical reasons however it is better to generate the hydrogen peroxide in situ. Preferably the hydrogen peroxide is produced enzymatically. Enzymatic production of hydrogen peroxide can be performed by using a number of different enzyme/substrate combinations, e.g. a combination of an oxidoreductase with an oxidizable substrate, for example:

glucose/glucose oxidase,

L amino acid/L amino acid oxidase, galactose/galactose oxidase, lactose/β-galactosidase/glucose oxidase, 2-deoxyglucose/glucose oxidase.

It is possible to add both the substrate and/or the oxidoreductase to the system which is to be protected. It is also possible to use an enzyme which is already present in the substance for which protection is sought. For example, in milk the normally present xanthine oxidase can be used to generate hydrogen peroxide by addition of hypoxanthine as a substrate. This addition of substrate is necessary to activate the system.

Combinations of different substrates and enzymes are equally effective and may give even better results. For example, the combination of glucose oxidase with β-galactosidase can be employed in lactose containing substances, β-galactosidase causes splitting of lactose, yielding galactose and glucose, the latter carbohydrate is then further oxidized by glucose oxidase.

The antimicrobial activity of this system is due to the formation of hypothiocyanate in the following reaction;

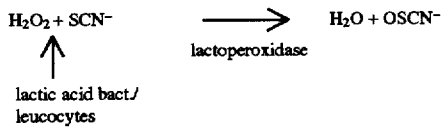

Raw milk contains all components which are essential for this reaction; thiocyanate and lactoperoxidase are present as such and hydrogen peroxide is produced by lactic acid bacteria or leucocytes. The thiocyanate is converted into hypothiocyanous acid (HOSCN) which at the pH of milk exists mainly in the form of the hypothiocyanate ion.

It may be useful in order to prolong the activity of the LP system to add hydrogen peroxide and/or if appropriate one of the other components of the system if they are limiting to the reaction. The addition of hydrogen peroxide in turn is limited by the effects which this molecule has on the activity of the lactoperoxidase and other proteins.

The hypothiocyanate ion reacts specifically with free sulfhydryl groups, thereby inactivating several vital metabolic enzymes and membrane proteins.

The hypothiocyanate has a bacteriostatic or bactericidal effect on a wide range of microorganisms. Activities of hypothiocyanate have been reported for example against, Pseudomonads, Enterobacteriaceae, Listeria, Yersinia, Campylobacter and Salmonella.

Milk preservation is an important application of this system. More generally, dairy products can be conserved using this system.

Other applications of the system in a more or less isolated form have been described. U.S. Pat. No. 4,320,116 describes the use of this system in animal feedstuff and a method for treating bacterial infections in the gastro-intestinal tract of mammals. Canadian patent application 1167381-A describes the use of this system in tooth-paste.

In general this system has the advantage of being food-grade; a wide spectrum of possible applications can therefore be envisioned.

One of the major problems with the use of the LP system is its short working time. The literature pertaining to this system thus far only reports activity ranging from a few hours to a maximum of a few days. The major factors responsible for this short working time are;

a) the uncontrolled (and high) production rate of hydrogen peroxide and, b) the high reactivity of the hydrogen peroxide. Due to its short working time, the LP system provides only temporary protection against microbial infection. The protected substances are prone to renewed contamination and therefore the use of the LP system has been limited to date, to short term protection.

There is a need for a long term protection of food and feedstuffs by a naturally occurring antimicrobial system. The present invention provides such a system.

SUMMARY OF THE INVENTION

The present invention discloses methods and means for increasing the working time of the lactoperoxidase system. To achieve this increased working time the invention discloses immobilized components of the lactoperoxidase system which provide for the sustained release of hydrogen peroxide. Sustained release of hydrogen peroxide makes steady and continuous production of hypothiocyanate possible.

The present invention discloses immobilized components of the LP system. A system is disclosed which gives hydrogen peroxide production for at least 42 days.

The invention further discloses the application of the immobilized lactoperoxidase system components in food and feed.

DETAILED DESCRIPTION OF THE INVENTION

Figure 1:
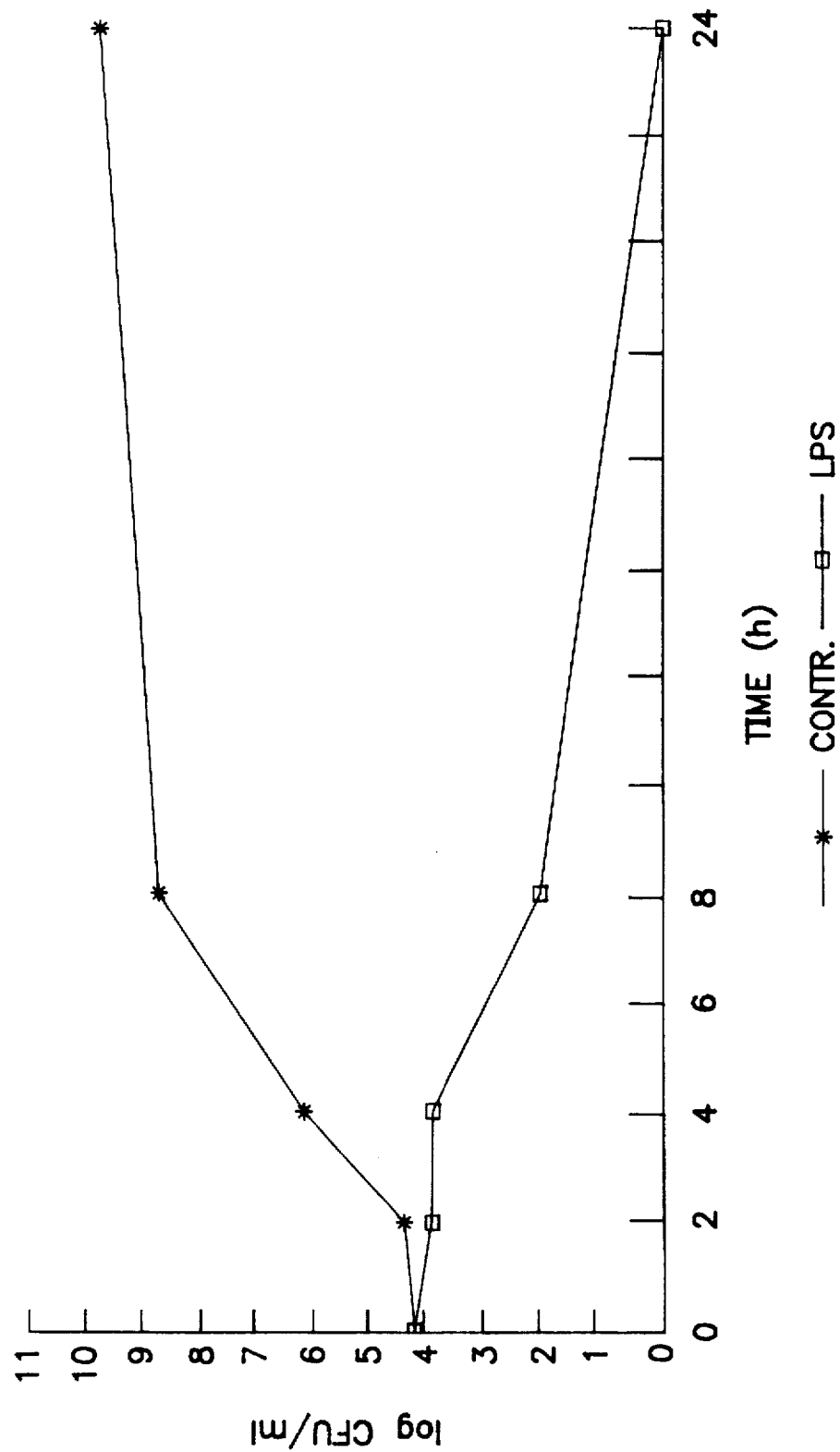
FIGS. 1–15 show the effect of the LP system on the following microorganisms: *Escherichia coli* ATCC 11229, *Salmonella typhimurium* ATCC 13311, *Bacillus cereus* IAM 1229, *Staphylococcus aureus* ATCC 6538 and *Listeria monocytogenes* RIVM 3 at the indicated pH values.

The present invention provides a composition for use in the sustained production of hydrogen peroxide comprising an oxidoreductase and or a corresponding substrate in an immobilized form.

In its most general form, the present invention provides a method for obtaining sustained release of hydrogen peroxide by use of the composition. The hydrogen peroxide is slowly released and may be used for its antimicrobial activity as such. In order to exhibit antimicrobial activity, the hydrogen peroxide must be present in relatively large amounts. Hypothiocyanate is a much more powerful antimicrobial agent than hydrogen peroxide. Antimicrobial activity has been reported for hydrogen peroxide at a concentration of 5 mM, whereas 0.02 mM hydrogen peroxide has been reported to activate the LP system. The hydrogen peroxide is therefore preferably used to convert thiocyanate into hypothiocyanate with the use of lactoperoxidase or another peroxidase.

Any thiocyanate salt may in principle be used. Commonly alkali metal salts such as sodium or potassium thiocyanate are used.

To obtain slow release of hydrogen peroxide at least one of the components of the hydrogen peroxide generating system is immobilized. This can be the enzyme (the oxidoreductase) and/or the substrate (glucose, galactose or other substrate) corresponding to the oxidoreductase used. It is also possible to immobilize more than one component.

The composition of the present invention may contain any oxidoreductase. Preferably the oxidoreductase is selected from the group consisting of glucose oxidase, L amino acid oxidase, galactose oxidase, β-galactosidase/glucose oxidase, xanthine oxidase with a corresponding substrate. Combinations of oxidoreductases may advantageously be used in the present invention.

In the present invention the hydrogen peroxide is made available continuously and preferably at a steady-state level high enough to activate the lactoperoxidase system. To achieve this the substrate may for example be present in a slowly soluble form or it may be present in polymer form in which case the substrate molecule is only available in usable form after an enzymatic or chemical reaction.

It is also possible to couple the above hydrogen peroxide production step with another reaction step in which the substrate is generated, thereby indirectly regulating the hydrogen peroxide production rate by regulating the substrate release or production rate. An example of this is glucose which is obtained from cellulose by reaction with cellulase. Another example is the degradation of lactose using the combination of glucose oxidase with β-galactosidase. Yet another example is the use of starch as a substrate necessitating the prior release of glucose. After release of the substrate the oxidoreductase reaction produces hydrogen peroxide. It has been found that immobilization of the components provides a prolonged glucose release rate.

The hydrogen peroxide thus obtained is preferably used for increasing the effective working time of the lactoperoxidase system. We focus our discussion on the lactoperoxidase system since this system is the system of choice for food applications. However, it is recognized that other enzymes can equally well be employed according to the present invention to generate hydrogen peroxide, for example horseradish peroxidase and chloroperoxidase.

Figure 19:
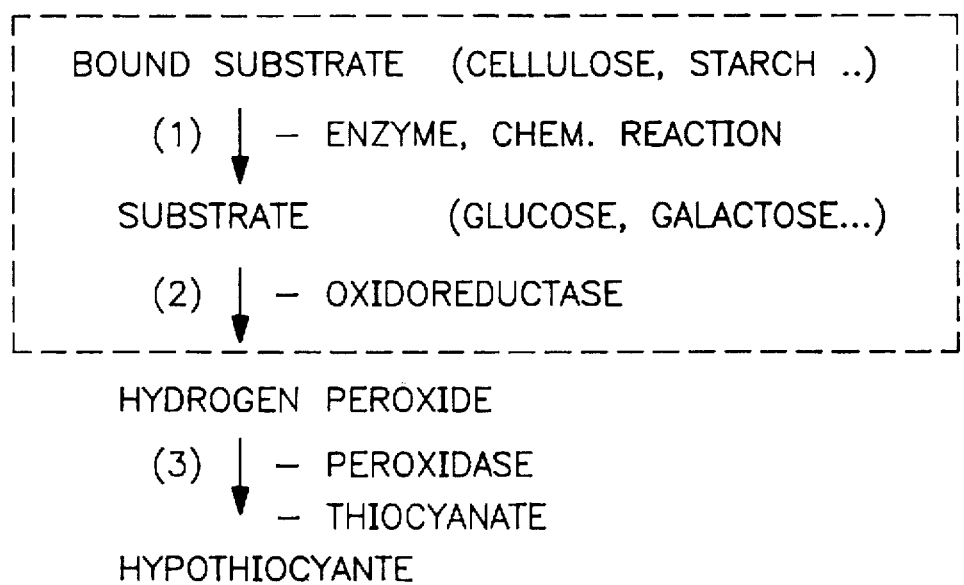
FIG. 19 shows a flow diagram for the system of the invention.

The system of the present invention can schematically be represented as shown in FIG. 19.

Encircled in FIG. 19 is the part of the system wherein at least one of the components is immobilized.

To our knowledge it has not previously been attempted to use the LP system to obtain prolonged antimicrobial protection. Prolonged antimicrobial activity solves at the same time the problem of possible recontamination.

To date the LP system is generally used to treat the substance once, and subsequent reinfection is avoided by physical separation of the 'protected' substance from sources of contamination.

The present invention makes outgrowth of reinfecting microorganisms during a longer period impossible.

In case the substrate used for the enzymatic reaction is also a substrate for one of the microorganisms present in the compositions to be protected, or in case the substrate is a substrate for other infecting microorganisms, it is preferable to add the substrate in a non-metabolisable form. Different options for using a non-metabolisable substrate present themselves;

1) the substrate can be immobilized, for example in the form of cellulose or starch. By producing and subsequently oxidizing glucose in situ, at a reaction rate that prevents accumulation, the growth of microorganisms can be prevented, 2) alternatively a non-metabolisable substrate as such can be employed; 2-deoxyglucose is an example.

The system of the present invention can be employed against a wide range of organisms. As indicated above the hypothiocyanate, which is produced in the lactoperoxidase reaction step, has been found to be active against a wide range of microorganisms including both gram-positive and gram-negative bacteria and fungi.

Activities of the hypothiocyanate have been reported for example against, Pseudomonads, Enterobacteriaceae, Listeria, Yersinia, Campylobacter, Salmonella, Streptococcus, Lactobacillus, Bacteroides, Flavobacterium and Fusobacterium.

The spectrum of activity of the present system can be increased by combining the system with other antimicrobial agents. Where apart from general protection, protection against a specific microorganism is required, it may be useful to add a bacteriocin to the system as described. This addition may be done either before or after immobilisation. Suitable bacteriocins are known and include lantibiotics such as nisin.

The present invention exemplifies the use of the LP system against both gram-positive and gram-negative bacteria. Specifically it is shown that the system of the present invention is effective against the following microorganisms: *Escherichia coli* ATCC 11229, *Salmonella typhimurium* ATCC 13311, *Bacillus cereus* IAM 1229, *Staphylococcus aureus* ATCC 6538 and *Listeria monocytogenes* RIVM 3. Tests with these microorganism have been performed at different pH between 5 and 7. At all values the system works well, the preferred pH was 6.3.

The present invention focuses on step (2), the second step of the three-step process described above, that is the hydrogen peroxide production step. In order to obtain a steady-state level of hydrogen peroxide the amount produced should be kept constant. To achieve a constant hydrogen peroxide production level, the substrate for the peroxide formation reaction can be added in a controlled manner. Alternatively a limiting amount of enzyme, with an excess of substrate can be used.

The invention provides a method for controllably and slowly generating the hydrogen peroxide, this is achieved by the immobilisation of the enzymes or the substrates. Immobilisation methods are known. Suitable methods make use of for example Calcium alginate, gelatin or carrageenan. If necessary the immobilized material can be reinforced by cross-linking agents.

In the present invention some of the possible compositions are exemplified. Avicel™ (cellulose) is immobilized together with cellulase and glucose oxidase in gelatin which is subsequently cross-linked with glutardialdehyde. In this system hydrogen peroxide is produced for at least 48 hours.

In another example cornstarch is immobilized together with α-amylase, amyloglucosidase and glucose oxidase in a combination of gelatin and alginate, with subsequent crosslinking with glutardialdehyde. It is shown that this system is capable of releasing hydrogen peroxide for at least 42 days.

It is understood that the amounts of the components and the composition itself in the system will vary depending on the specific application. The coupling of the exemplified systems with lactoperoxidase/thiocyanate will increase the effectivity of the antimicrobial composition.

In liquid form minimal amounts of the LP components are as follows;

glucose oxidase (Gist-brocades) 0.8 mg/l,
lactoperoxidase (Biopole) 1 mg/l,
hydrogen peroxide 0.02 mM,
SCN 0.02 mM.

In general the molar ratio between peroxide and thiocyanate is smaller than 4 and preferably it is 1–2. The lactoperoxidase is present in amounts varying from 1–200 mg/l. Activities of the enzymes are as follows; glucose oxidase, 36.000 units/g (pH=6, T=14° C.), wherein 1U=1 μmol hydrogen peroxide /min, lactoperoxidase 481.000 ABTS units/g (pH=6, T=25° C.) (ABTS method, Childs et al. Biochem.J. (1975) 145 93–103).

Finally the present invention discloses a food product which when treated with $10^2$–$10^5$ microbial cells per g between 2–10 days after preparation and which is subsequently kept at normal growth conditions for the infecting microorganism does not give rise to outgrowth of this microorganism and wherein protection is due to sustained hydrogen peroxide production. Specifically, it is also shown that the LP system is effective against Listeria, when applied on cheese (Camembert).

Specific amounts of cells and growth conditions may of course vary depending on the nature of product and the microorganism which is employed.

When practising the invention, the substance to be protected is mixed with quantities of the reagents in such a ay that the hydrogen peroxide will be generated in such an mount per unit time that a steady-state concentration is achieved.

The system as described, provides its antimicrobial protection for at least 10 days, preferably at least 20 days and more preferably up to 50 days.

Utility of the Invention

The system can be applied to food and feed conservation. With respect to this application, it can be used in a liquid, for example in (cheese-)milk, but it will be equally effective when applied to the surface of for example cheese. The system can also be applied as a longterm cleaning agent in specific applications. It is understood that the amounts of the components in the system will vary depending on the specific application.

The use of this system can be envisioned in the decontamination of carcases (bovine, fish, shrimps), surface treatment of food (cheese, butter), treatment of fresh vegetables, cosmetics, wound treatment, toothpaste, decontamination of machines (icemachines, milkshake machines) or more broadly equipment used in food processing in plants or in area wherein food is prepared in large amounts (hospitals, restaurants and the like), decontamination of udders, silage and in feedstuff.

EXPERIMENTAL

Hydrogen Peroxide Analysis

Measurement of the amount of hydrogen peroxide was performed by a modification of the method described Mottola et al. Anal. Chem. 42:410–411 (1970).

Briefly, in a 1 cm cuvet the following solutions were mixed;

50 μl sample containing hydrogen peroxide (0.2–1 mM)

200 μl leuco-crystal-violet (LCV) solution (0.5–1 mg/ml in 0.5% HCl)

1.6 ml Sodium acetate buffer (0.5 mM pH 4.5)

100 μl lactoperoxidase (2 mg/ml) or HRP (Horse Radish Peroxidase)

In the presence of thiocyanate, lactoperoxidase can not be used to obtain accurate measurements in this assay. However, under these conditions horse radish peroxidase works well.

Color development was followed at 596 nm.

Composition of Media

Minimal medium contained the following substances per liter; $K_2HPO_4$, 14 g; $KH_2PO_4$, 6 g; $(NH_4)SO_4$, 2 g; Trisodiumcitrate. $2H_2O$, 1 g; $MgSO_4$. 7 $H_2O$, 0.2 mg; $MnSO_4$. $2H_2O$, 5 g; L-glutamic acid, 2 g; NaOH, 0.8 g; 50 ml 10% Casamino acid solution (Difco), 20 ml 50% glucose solution and 10 ml Vitamin solution.

Vitamin solution contained per liter; 2 mg biotin; 2 mg folic acid; 10 mg pyridoxine HCl B6; 5 mg thiamine HCl B1; 5 mg riboflavin B2, 5 mg nicotinic acid; 0.1 mg vitamin B12; 5 mg p-aminobenzoic acid; 5 mg DL Calciumpenthotenate. Cheese milk medium (CM medium) contained per liter; 15 g Caseinehydrolysate, 3 g tri-sodiumcitrate, 3 g lactose, 3.5 g lactate, 5 g tryptose and 50 mM phosphate buffer (pH 5, 6 or 7). After sterilisation glucose was added.

EXAMPLES

Example 1
Activity of the Lactoperoxidase System Against Specific Microorganisms The activity of the lactoperoxidase system against five different microorganisms was tested using glucose oxidase/glucose to generate hydrogen peroxide.

The microorganisms used were the following:

Gram-negative: *Escherichia coli* ATCC 11229 *Salmonella typhimurium* ATCC 13311

Gram-positive: *Bacillus cereus* IAM 1229 *Staphylococcus aureus* ATCC 6538 *Listeria monocytogenes* RIVM 3

*E.coli*, *S.tyhimurium*, *B.cereus* and *S.aureus* were incubated at the desired pH in minimal medium.

*L.monocytogenes* was incubated in cheese milk medium. After overnight culture the cells were used to inoculate the main culture to a density of $10^3$–$10^5$ cells/ml. The incubation temperature was 37° C. The pH was 5.2, 6.3 or 7.2 (for *L.monocytogenes*; 5.0, 6.0 and 7.0). To these cultures the given substances were added to the indicated final concentrations:

SCN 100 mg/l (sodium salt, Merck)

lactoperoxidase 20 mg/l (Biopole);

glucose-oxidase 1.5 mg/l (Gist-brocades);

glucose 10 g/l (BDH).

The control cultures contained the same substances without glucose-oxidase.

The number of viable cells was followed in time and determined by plating several dilutions on BHI plates.

The hydrogen peroxide concentration was monitored during these experiments using the method outlined in Experimental. It could be concluded that using the concentrations mentioned above the hydrogen peroxide was never present in an amount sufficient to have any microbial effect as such. Thus, the antimicrobial effects described could completely be attributed to the hypothiocyanate. Results are shown in FIGS. 1–15.

Figure 2:
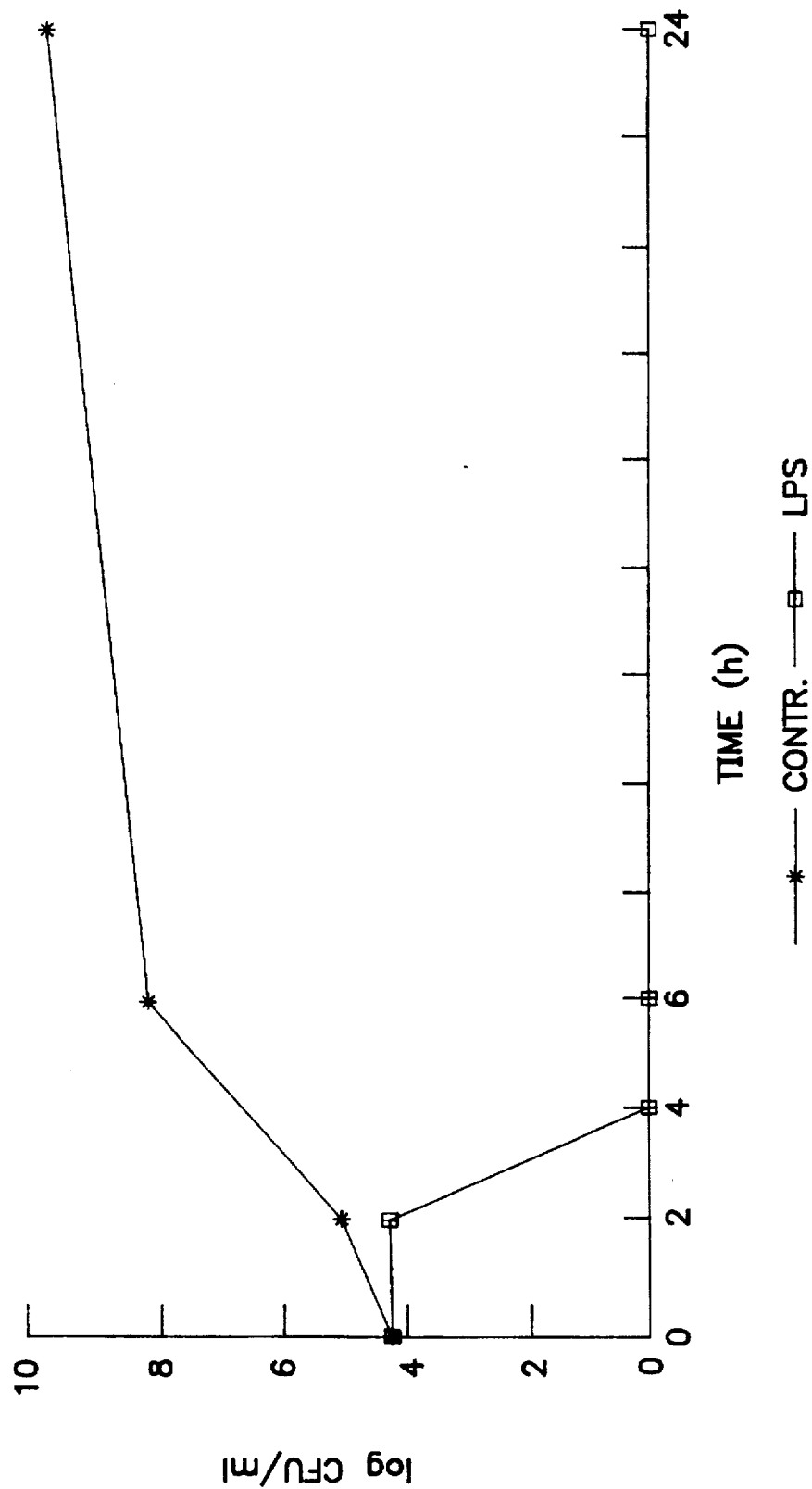
Figure 3:
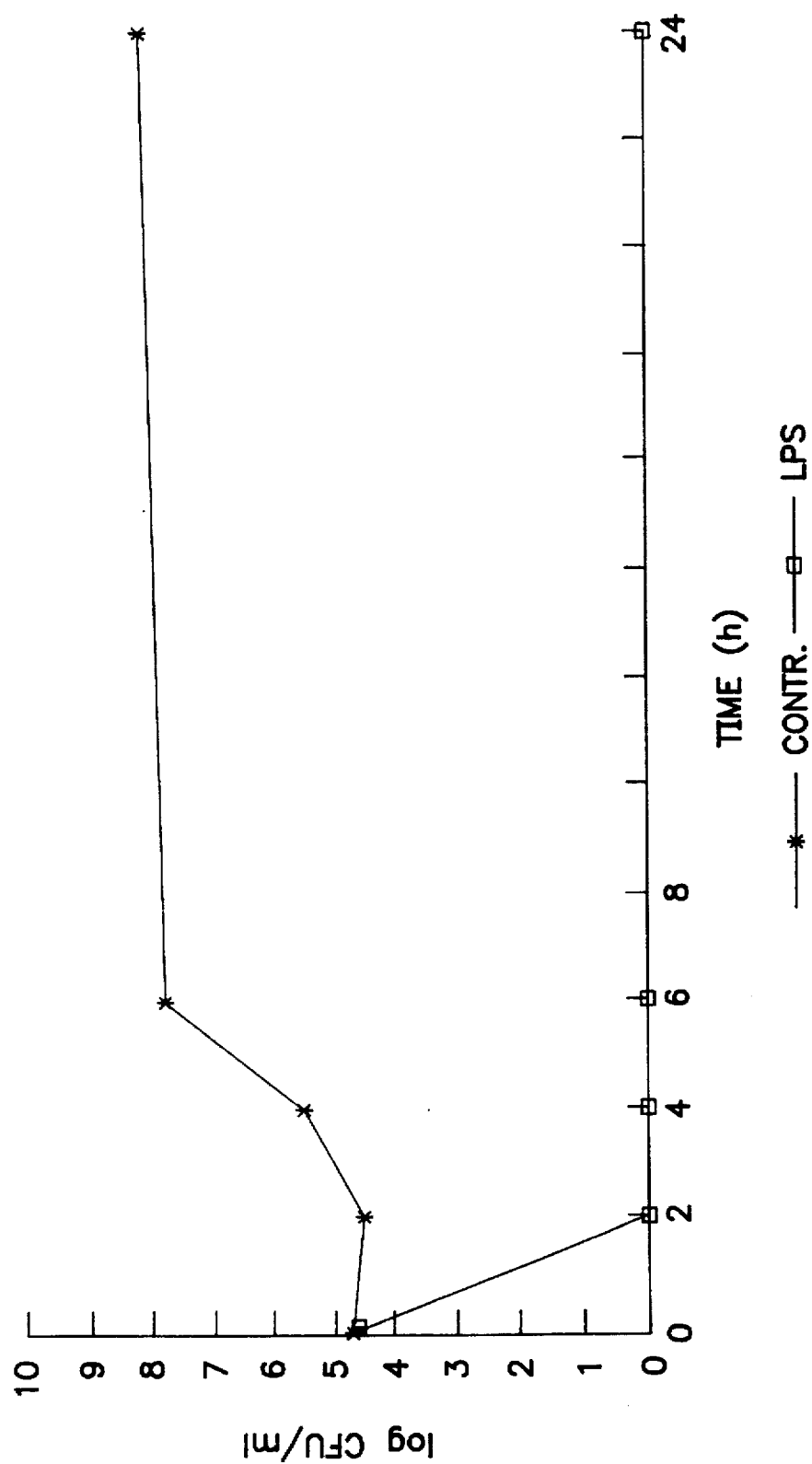

*E. coli* (FIG. 1–3)

| | |
|---|---|
| pH = 7.2 | cells killed between 8 and 24 hours control continues to grow after a lag phase of 4 hours |
| pH = 6.3 | cells killed after 4 hours control continues to grow after 4 hours |
| pH = 5.2 | cells killed after 2 hours control continues to grow after 6 hours |

Figure 4:
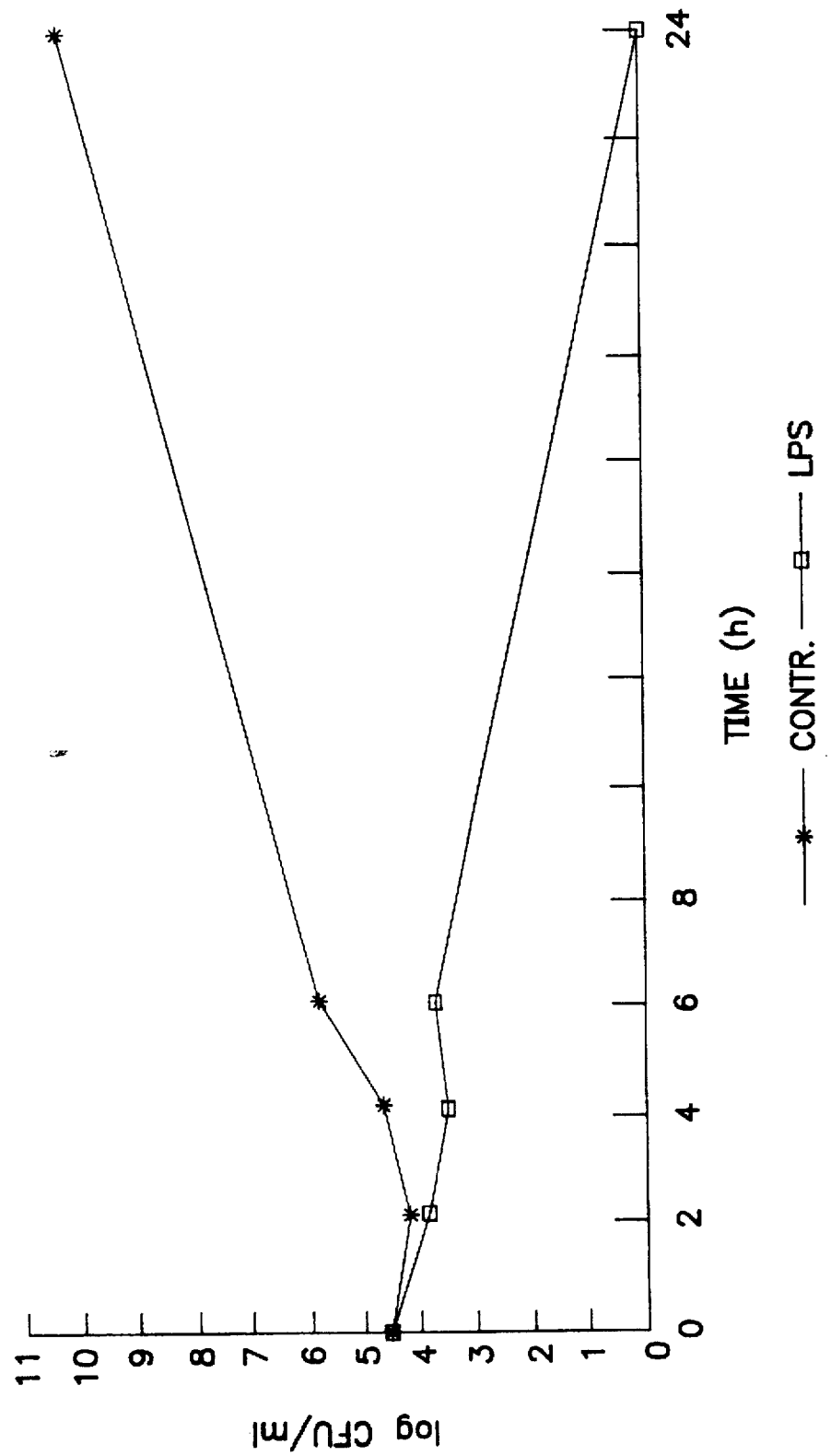
Figure 5:
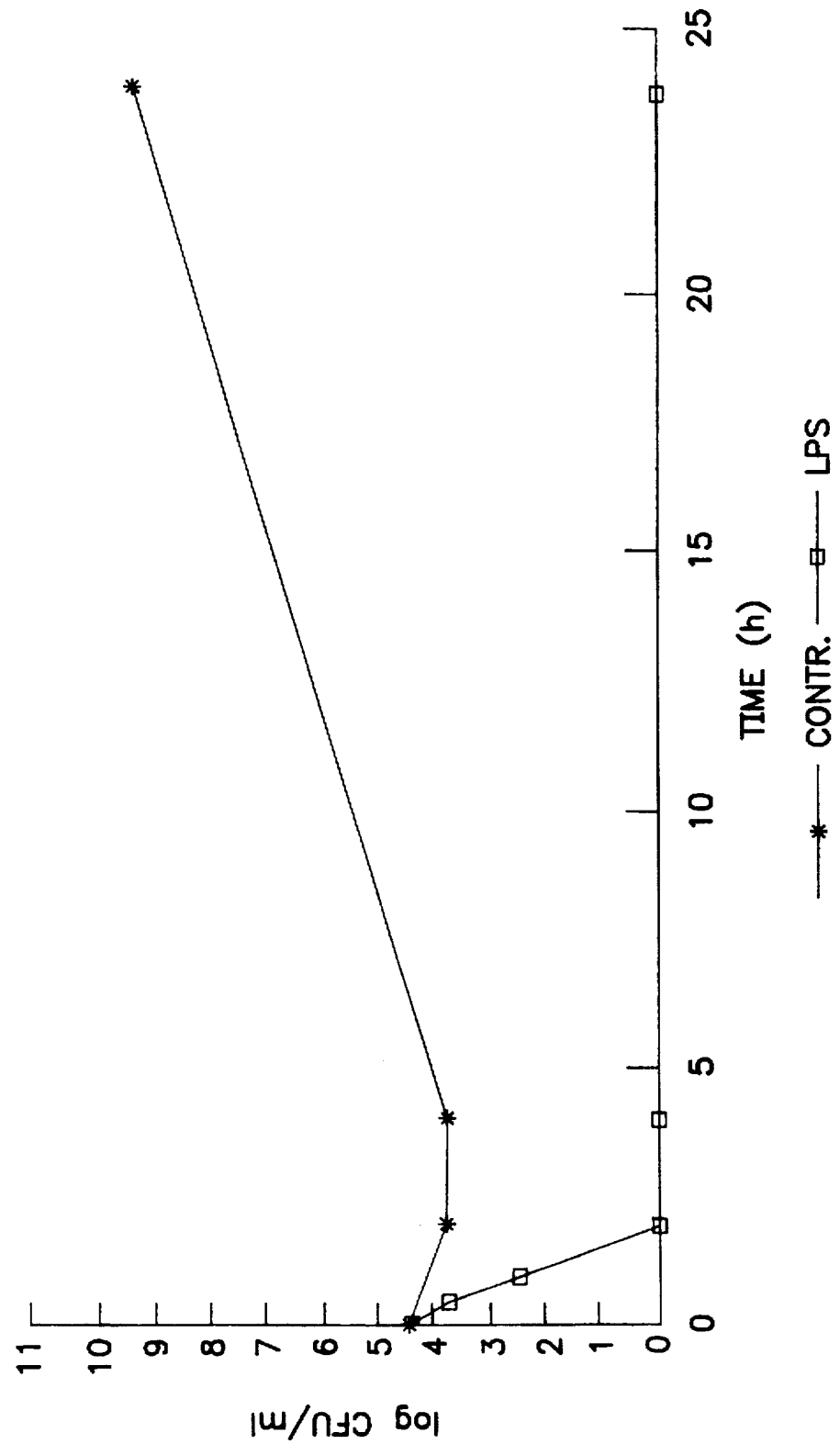
Figure 6:
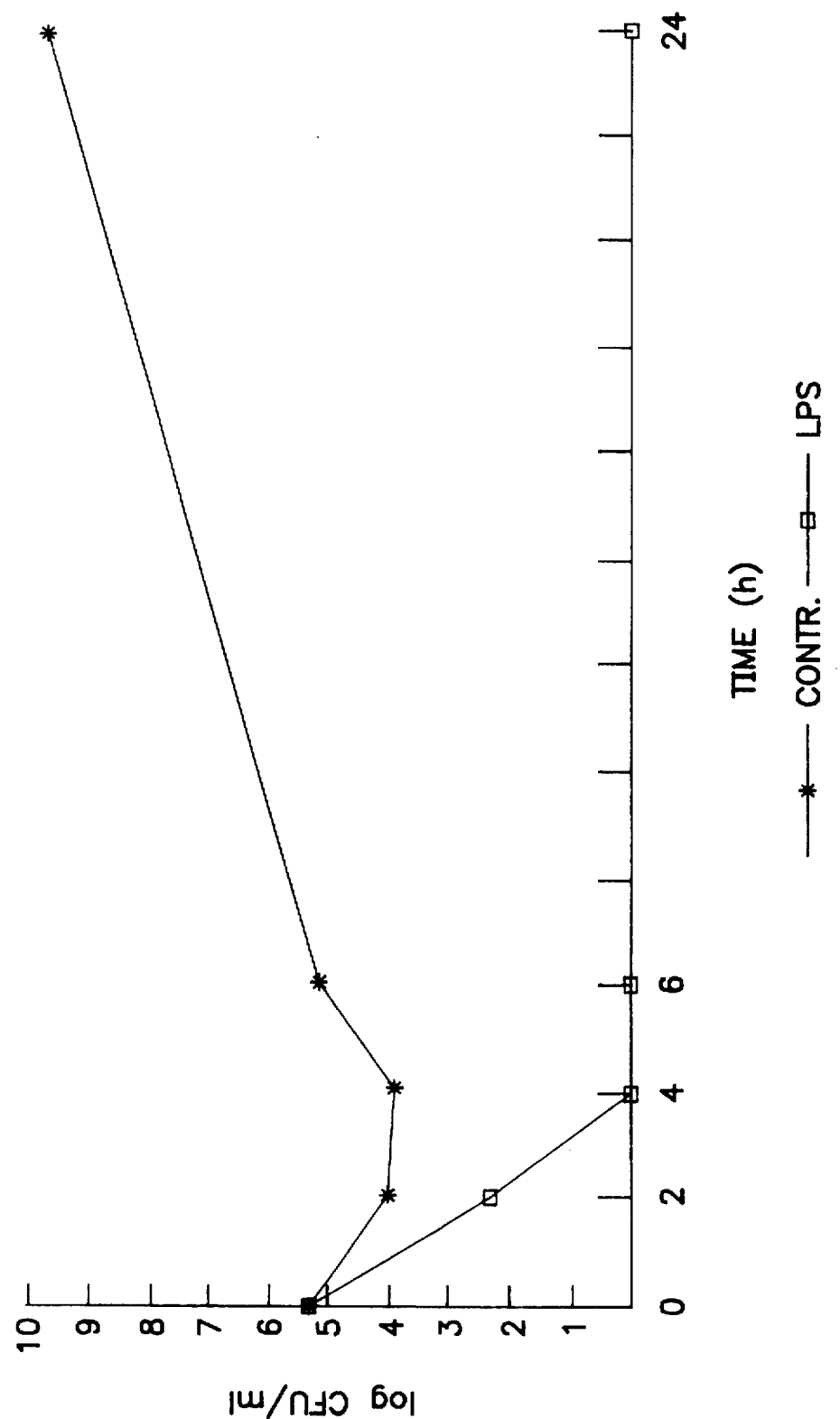

*S. typhimurium* (FIG. 4–6)

| | |
|---|---|
| pH = 7.2 | cells killed between 6 and 24 hours control continues to grow after 4 hours |
| pH = 6.3 | cells killed within 2 hours control continues to grow after 6 hours |
| pH = 5.2 | cells killed after 4 hours control continues to grow after 4 hours |

Figure 7:
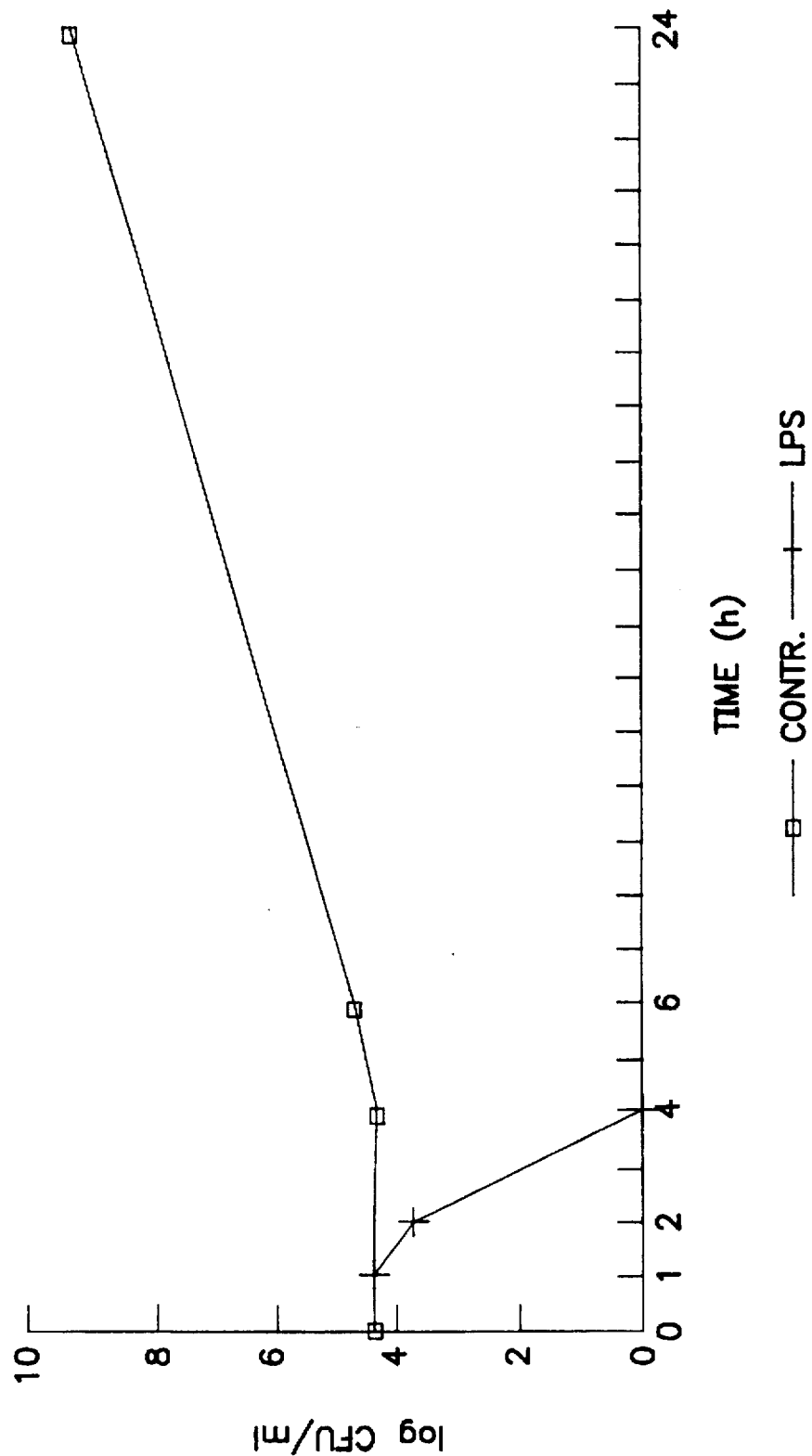
Figure 8:
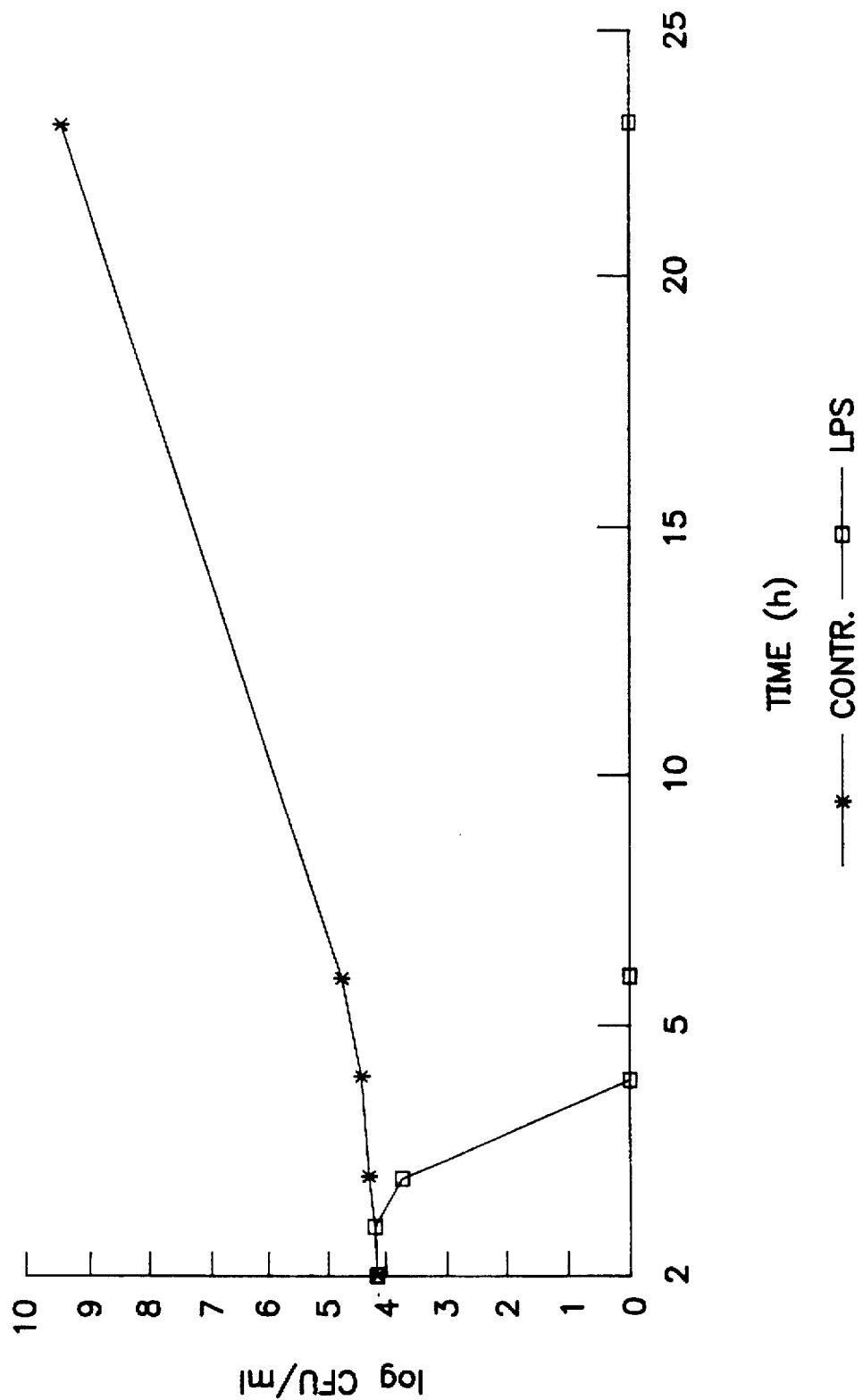
Figure 9:
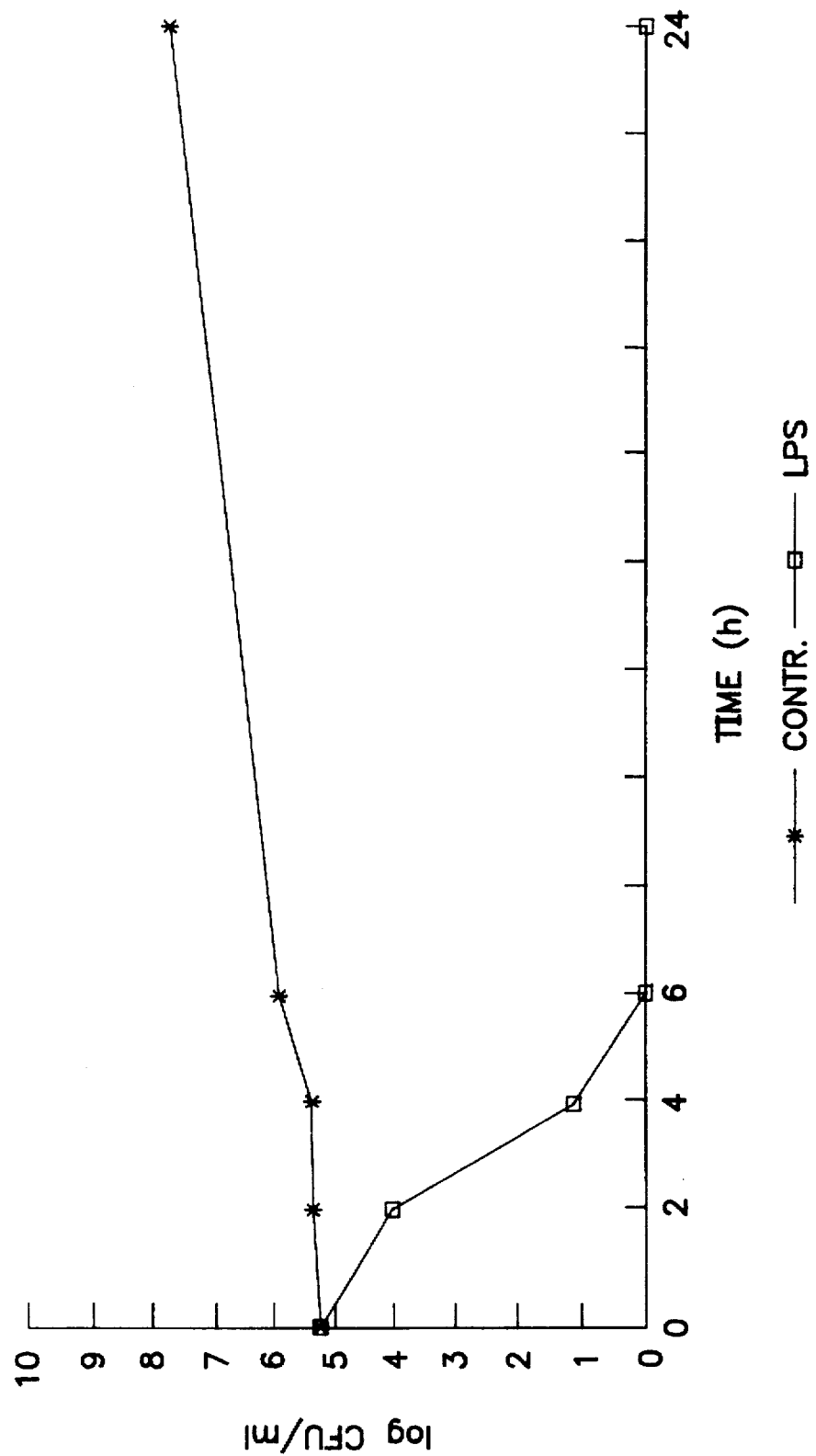

*S. aureus* (FIG. 7–9)

| | |
|---|---|
| pH = 7.2 | cells not completely killed control continues to grow after 8–24 hours |
| pH = 6.3 | cells killed within 4 hours control as with pH = 7.2 |
| pH = 5.2 | cells killed within 6 hours control as with pH = 7.2 |

Figure 10:
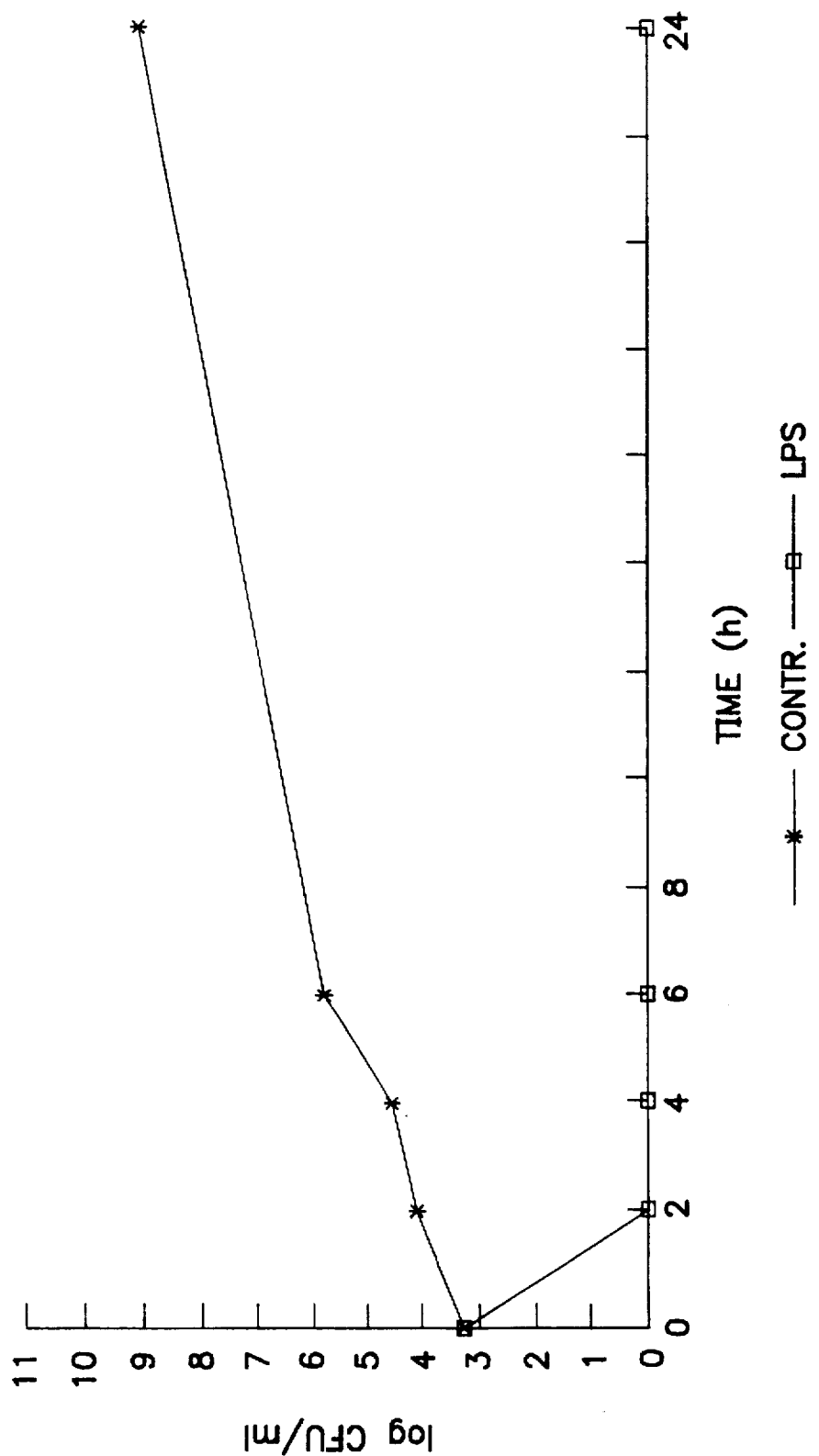
Figure 11:
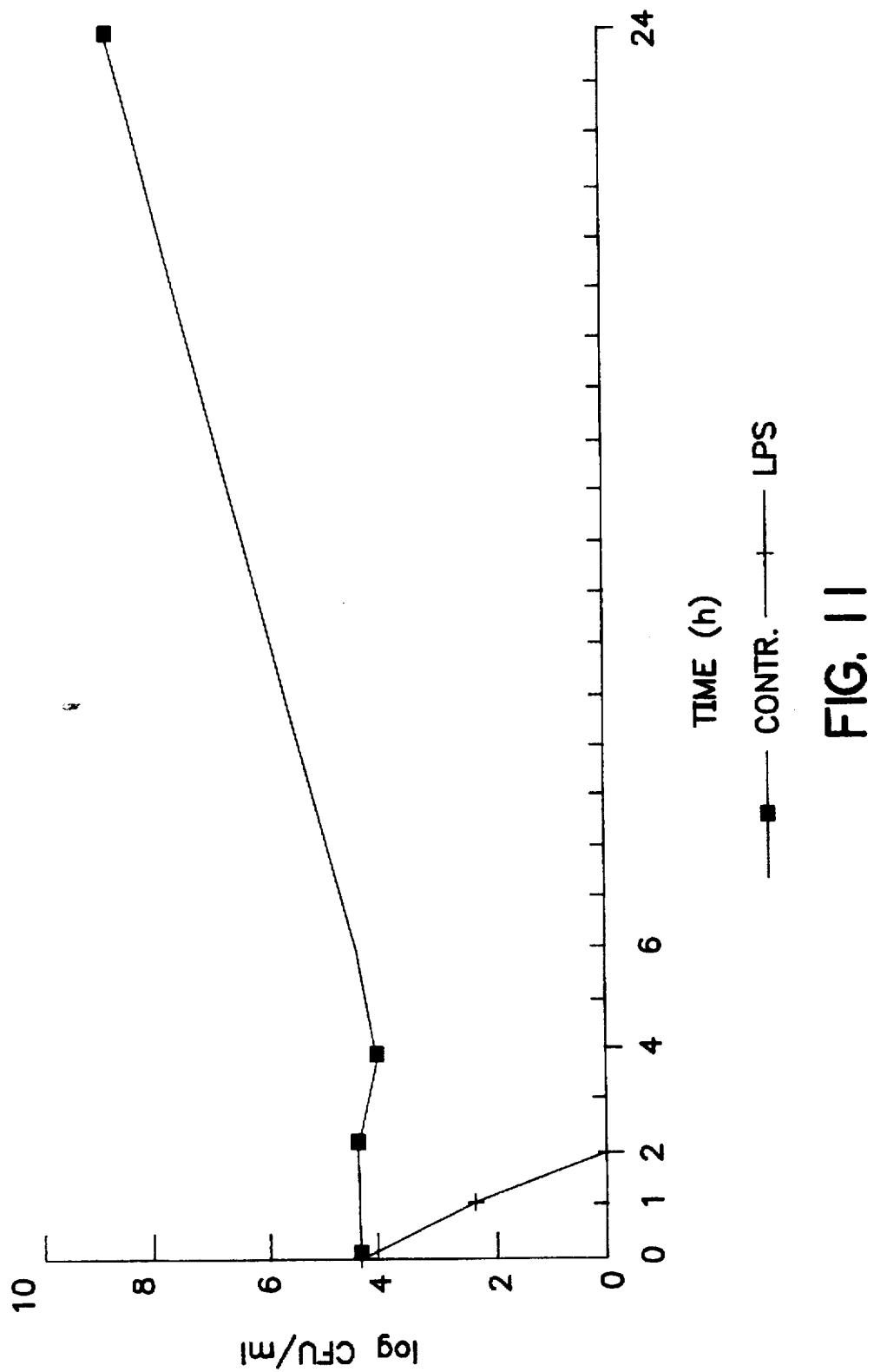
Figure 12:
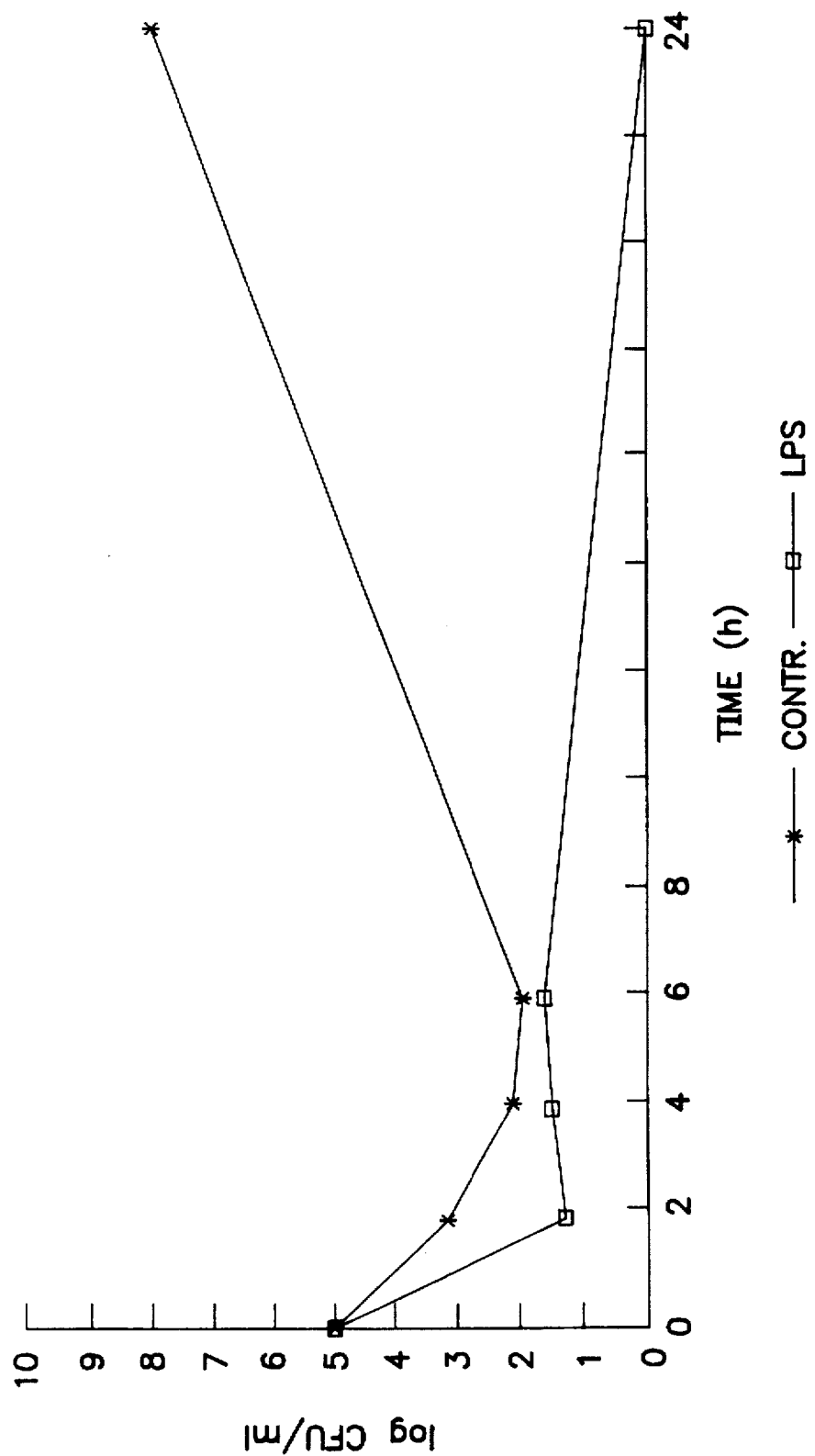

*B. cereus* (FIG. 10–12)

| | |
|---|---|
| pH = 7.2 | cells killed within 2 hours control continues to grow after 2 hours |
| pH = 6.3 | cells killed as with pH = 7.2 control continues to grow after 4 hours |
| pH = 5.2 | cells killed between 6 and 24 hours control continues to grow after 6 hours |

Figure 13:
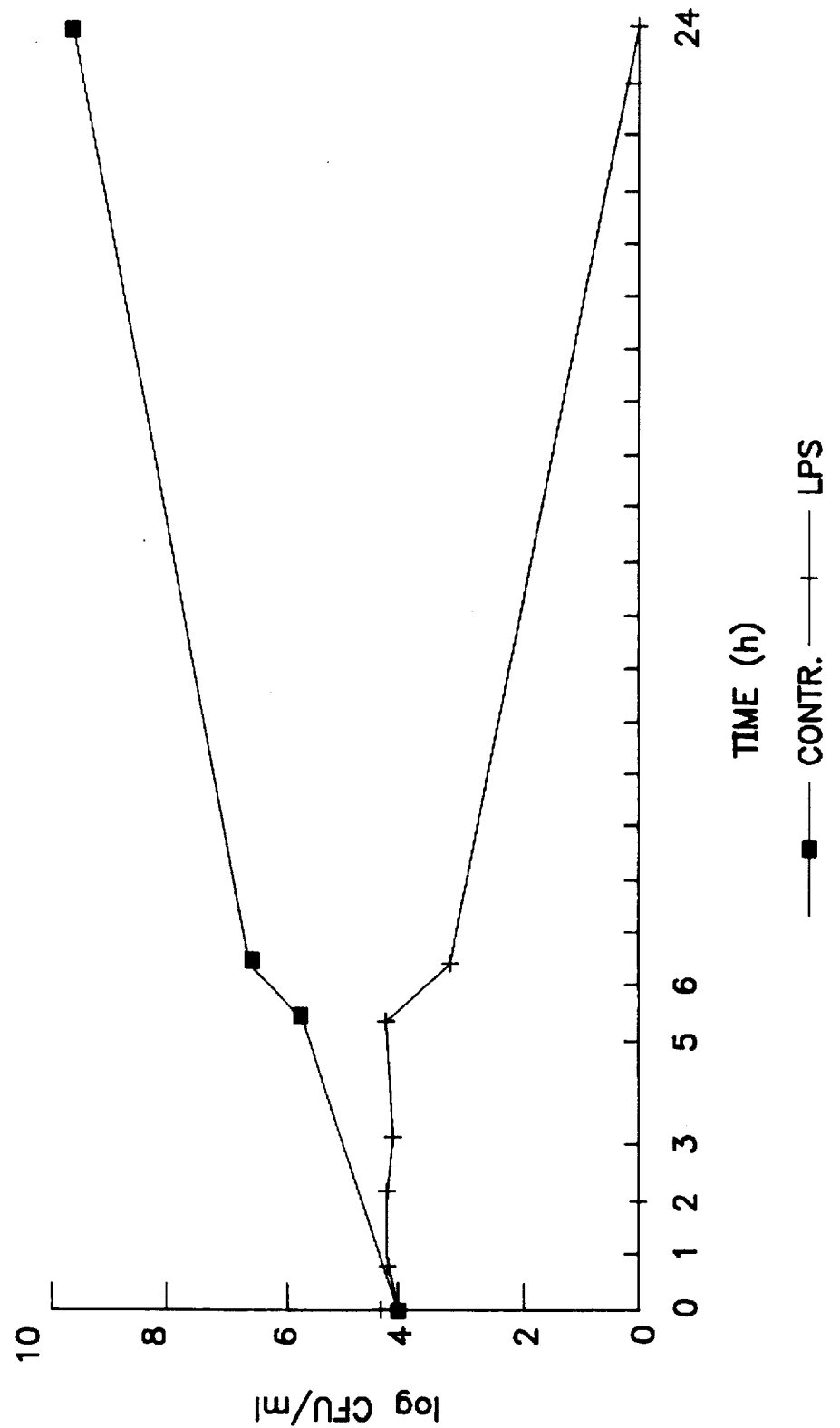
Figure 14:
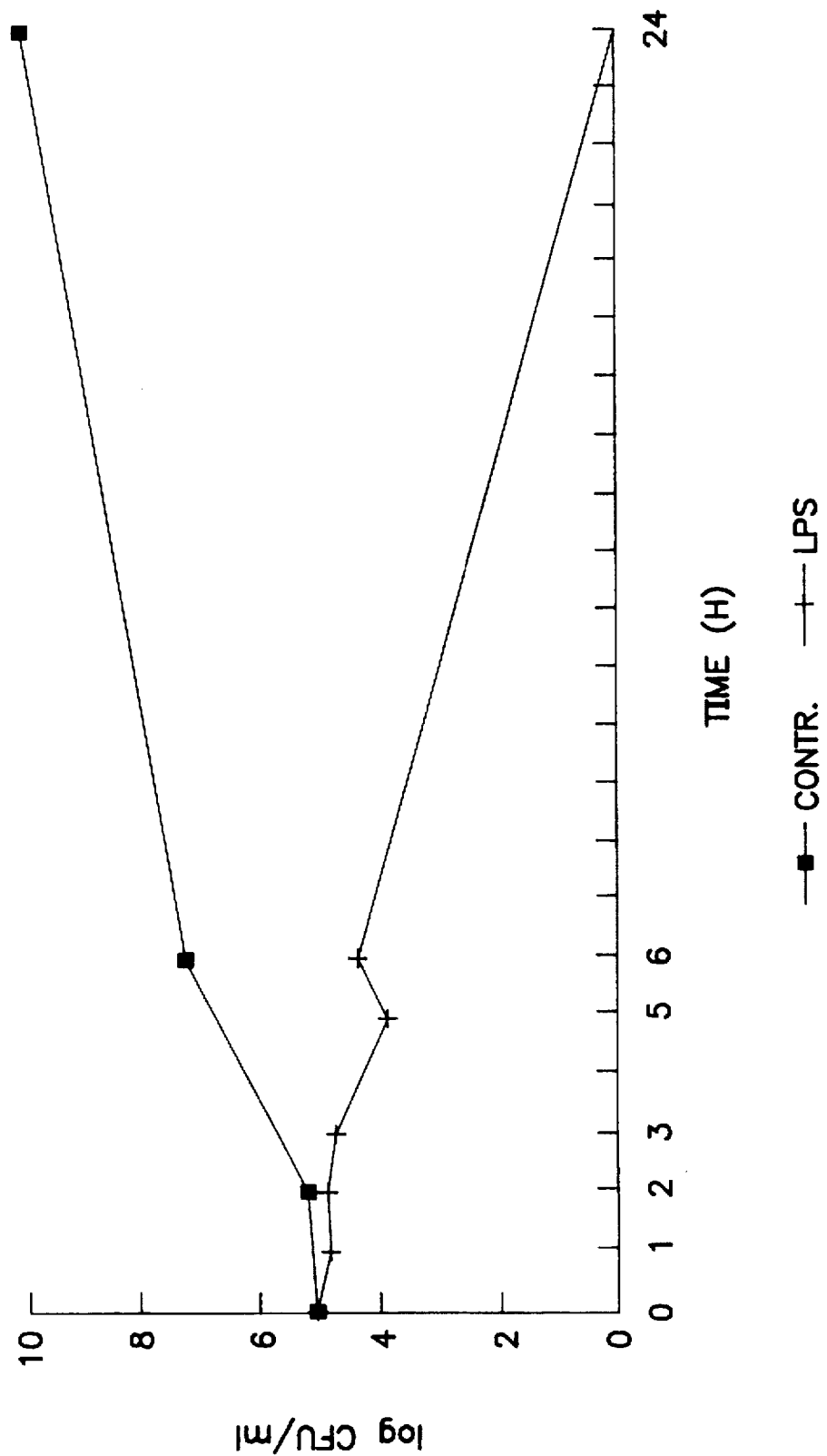
Figure 15:
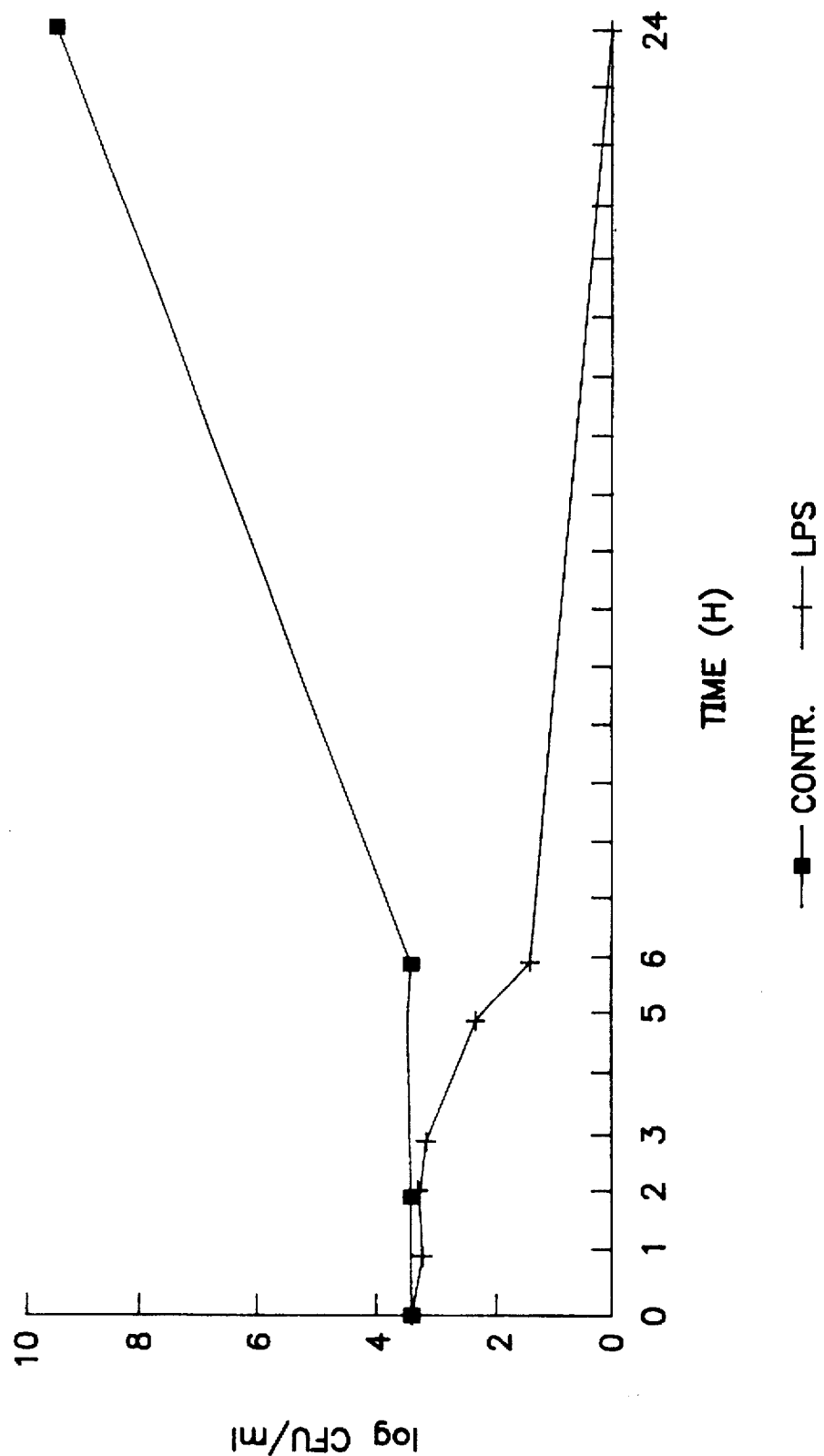

*L. monocytogenes* (FIG. 13–15)

| | |
|---|---|
| pH = 7.0 | cells killed between 5 and 24 hours control continues to grow after 5 hours |
| pH = 6.0 | cells killed between 3 and 24 hours control continues to grow after 2 hours |
| pH = 5.0 | cells killed between 3 and 24 hours control does not grow at this pH. |

It can be concluded that all tested microorganisms are adequately killed under the given experimental conditions, except for *S.aureus* at pH=7.2. Overall pH=6.3 is the optimal pH.

Example 2
Sustained Release of Hydrogen Peroxide 5 g of Avicel™ (a crystalline polymer conststing of cellulose, Serva) was suspended in 45 ml of an aqueous solution of gelatin, at 30° C. Subsequently 20 mg cellulase (Gist-brocades, Maxazym™ CL 2000) and 25 mg glucose oxidase (Gist-brocades) were added. This gelatin-polymer-enzyme suspension was added to 100 ml of a stirred cornoil (Brocacef) solution at 30° C. The water in oil suspension was cooled to 10° C. The particles are cross-linked by slowly adding (in 60 min) 1.03 g glutardialdehyde (Merck) in 8.25 ml water.

0.05 g Tween 80 in 5 ml water was added and stirring was continued for 5 min.

Subsequently the particles were separated from the oil phase by addition of 1000 ml water and the particles were washed twice with the same amount of water. The particles were stable and insoluble in water.

The release of hydrogen peroxide was followed in time using the method described in the Experimental section. The experiment was performed by incubating 5 g of the particles in 50 ml buffer (pH=5.0) in a stirred reactor vessel at room temperature.

The results are shown in Table 1. It can be concluded that hydrogen peroxide production is sustained and constant.

TABLE 1

| | Generation of hydrogen peroxide | |
|---|---|---|
| time (h) | µmol $H_2O_2$ | /h/g particles |
| 24 | 0.020 | 0.021 |
| 48 | 0.022 | 0.019 |

Example 3
Effect of the Lactoperoxidase System on Camembert Cheese Infected with Listeria Monocytogenes Camembert cheese frozen 1 day after production was kept frozen at −50° C. Freezing and thawing had no visible effect on the cheese flora. Cheeses were put in refrigerator boxes with a volume of 1 liter and the relative humidity was kept at 95% using a glycerol/water mixture.

The boxes were incubated at 14° C. After 5 days cheeses were treated with *Listeria monocytogenes* DSM 20600 at 100 cells per gram cheese (in 0.5 ml). After 4 hours the cheeses were treated at one side with 0.6 ml of LPS solution (100 mM glucose (BDH), 20 mM NaSCN (Merck), 200 mg/l lactoperoxidase (Biopole) and 50 mg/l glucose oxidase (Gist-brocades)). Control cheeses were treated with milli-Q water.

The number of Listeria were counted at t=0 and after 1, 2 and 5 days in duplo. Counting was performed by diluting 17 g of cheese two times in 2% tri-sodiumcitrate. After homogenisation in a Stomacher the suspension was diluted in a physiological salt solution.

0.1 ml of different dilutions were brought onto Palcam plates (Merck). Plates were grown at 30° C. during one day and colonies were counted.

Figure 16:
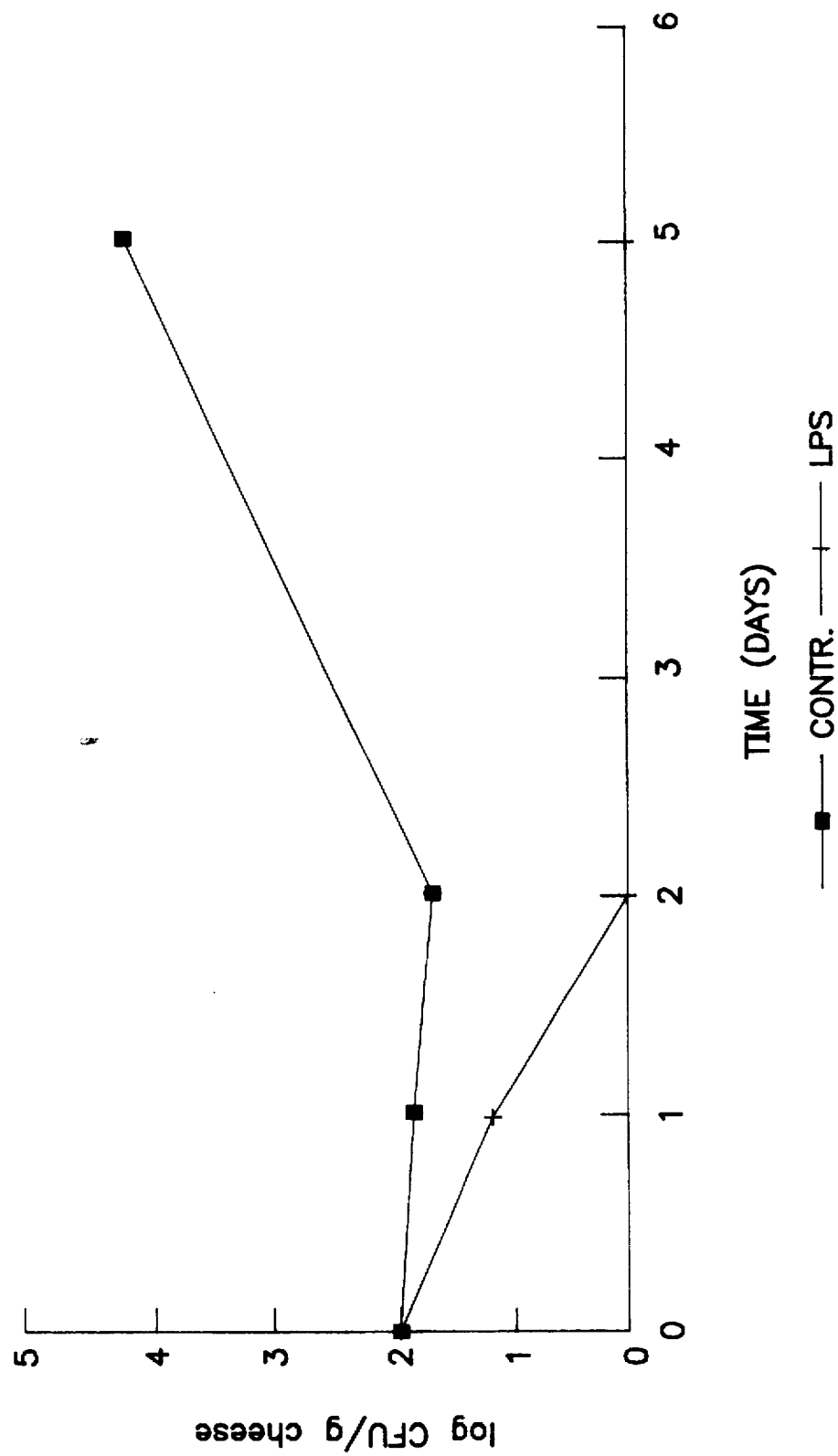
FIG. 16 shows the effect of the lactoperoxidase system on Camembert cheese infected with Listeria.

The result is shown in FIG. 16 and it can be concluded that the LPS system works well under application conditions.

Example 4
Use of Immobilized Cornstarch as a Glucose Source I

A suspension consisting of 10% (w/w) cornstarch in 8% (w/w) gelatin and 1% (w/w) alginate was prepared. The mixture was kept at 30° C. and 0.05% α-amylase (Gist-brocades, Maxamyl™, 6300 TAU/g), 0.05% amyloglucosidase (Gist-brocades, Amigase™ TS, 25000 AGI/ml) and 0.05% glucose oxidase (Gist-brocades) (all on w/w basis) were added.

Subsequently the suspension was poured into two volumes of cornoil containing 1% (w/w) Span 80. The mixture was heavily stirred using a turbin rotor. After 5 minutes the temperature was lowered to 15° C. and after coagulation 8.25 ml cross-link mixture was added per 50 g of formulation. Cross-link mixture consisted of 88.5% $CaCl_2 \cdot 2H_2O$ in ethanol (40 g per 100 ml ethanol) and 11.5% glutaraldehyde (25% w/w). After 60 minutes the immobilisation product-oil emulsion was stirred in an excess water for 5 minutes and the oil was decanted. The immobilisation product was subsequently washed twice with an excess of water and finally isolated by fractionated sieving.

In order to follow the hydrogen peroxide production rate production of gluconic acid was measured. Gluconate is a product of the hydrogen peroxide forming reaction:

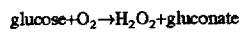

Two open, stirred 100 ml reaction vessels were used to follow the D-gluconic acid production at room temperature. Vessel one contained 2.5 g of immobilisation product in 25 ml 0.1M sodium acetate buffer, pH 5. Vessel two contained 0.277 g glucose and 1.38 g glucose oxidase in 25 ml 0.1M sodium acetate buffer, pH 5. D-gluconic acid was measured using an enzymatic test kit from Boehringer Mannheim (cat. no. 428.191).

Figure 17:
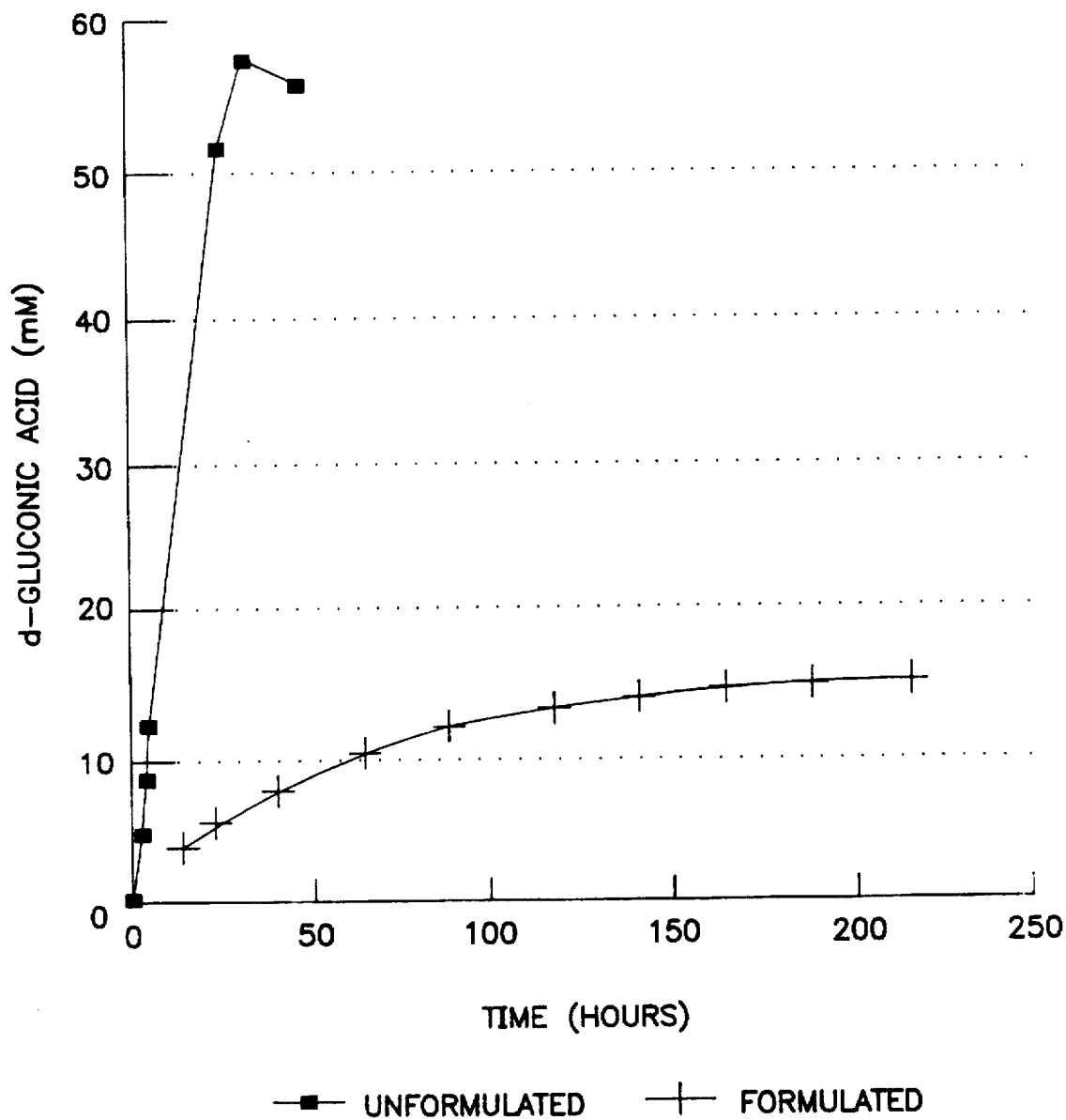
FIG. 17 shows the production of d-gluconic acid in time from free glucose and from immobilized cornstarch.

The results are presented in FIG. 17 it can be seen that without immobilisation and use of free glucose the D-gluconic acid production stops after about 50 hours whereas D-gluconic acid production and hence hydrogen peroxide production continues for more than 200 hours when immobilized starch is used as glucose source.

The maximum amount of gluconic acid which could be obtained from the amount of starch used in this experiment was 60 mM.

Example 5
Use of Immobilized Cornstarch as a Glucose Source II 50 g of cornstarch was suspended in 200 ml water and heated to 85° C. The slurry was kept at this temperature for 15 minutes with continues stirring. A solution of 50 g gelatine in 200 ml was added. After cooling the suspension to about 40° C., 125 mg amyloglucosidase (Amigase™ TS), 250 mg glucose oxidase and 1250 mg lactoperoxidase were added. Thereafter 6 ml glutardialdehyde (25% w/w) was added with continuous stirring. The gel was homogenized with a blender. After homogenization 2 1, 0.2M sodium acetate containing 0.7% glutardialdehyde was added. The mixture was stirred for 15 minutes at 15° C. The product was sieved and washed twice with a tenfold volume of water. The product was subsequently dried in a fluid bed dryer at 39° C. to 94% (w/w) dry weight. Finally the dried particles were milled in a high speed hammer mill to a particle size of approximately 20 microns.

150 mg of the dried particles (20 microns) was suspended in 149 ml 0.1M sodiumphosphate buffer pH=7.5, containing 4.5% (w/v) NaCl and 1.0 ml 400 mM NaSCN.

Figure 18:
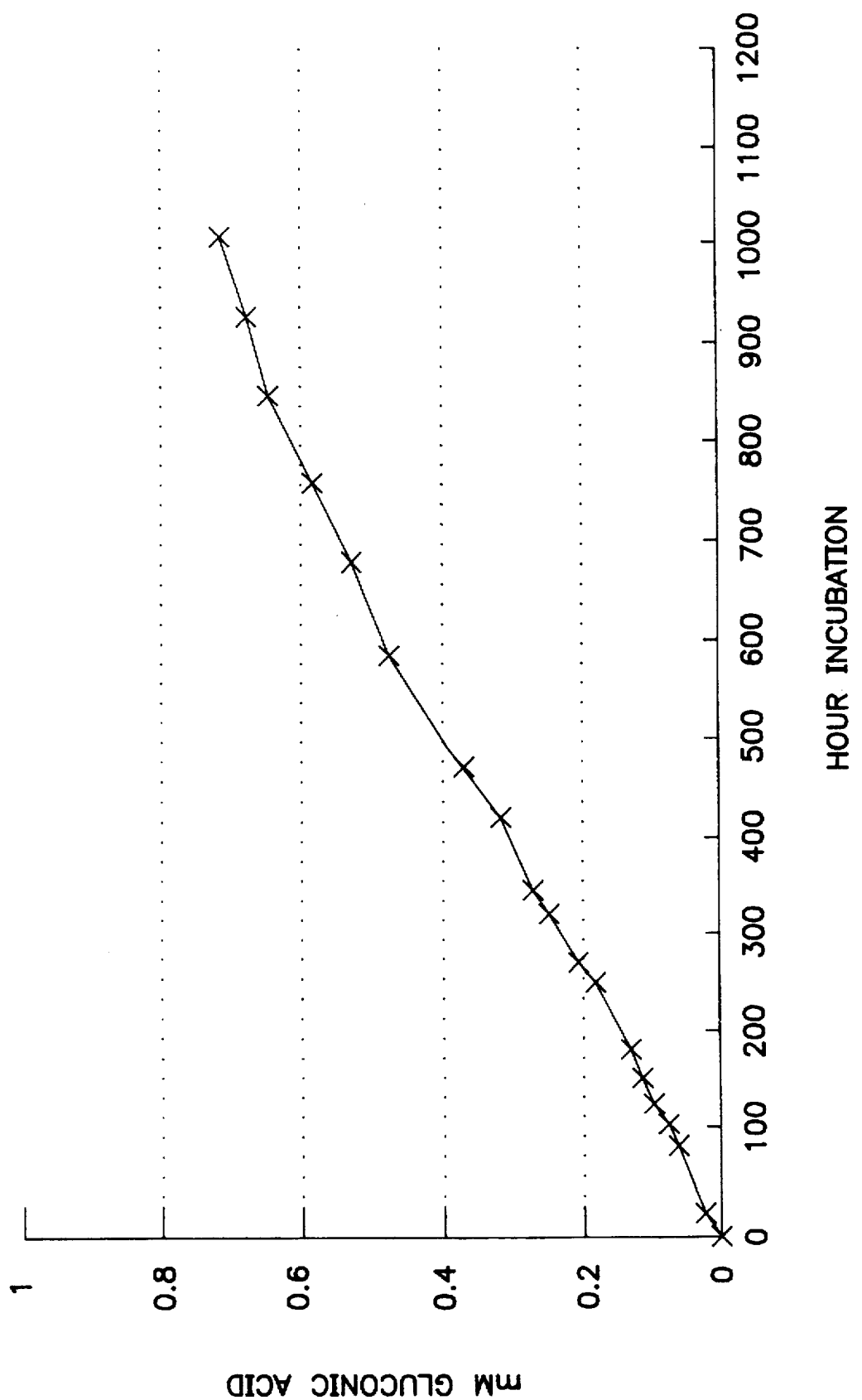
FIG. 18 shows the production of gluconic acid in time using immobilized cornstarch.

Incubation was in a shaking waterbath at 7° C. with such a speed that the particles were kept in constant motion and that aeration was assured. Gluconic acid production was followed in time using the previously mentioned Boehringer test kit. FIG. 18 shows the results. Under the given conditions hydrogen peroxide can be generated for at least 42 days at a constant rate.

The maximum amount of gluconic acid which could be obtained from the amount of starch used in this experiment was 3 mM.

We claim:

1. A food product comprising an immobilized composition containing at least one first enzyme which is an oxidoreductase that generates hydrogen peroxide from a substrate;

a second enzyme which is capable of generating said substrate from a precursor; and a precursor for said second enzyme wherein said first and second enzymes and said precursor are together immobilized in said composition with an immobilizing agent.

2. The food product of claim 1 wherein the oxidoreductase is selected from the group consisting of glucose oxidase, L-amino acid oxidase, galactosidase and xanthine oxidase.

3. The food product of claim 1 wherein the second enzyme is amyloglucosidase, α-amylase, or a mixture of amyloglucosidase and α-amylase and the precursor is starch.

4. The food product of claim 1 wherein the immobilizing agent comprises alginate, gelatine or carrageenan.

5. The food product of claim 1 wherein at least two oxidoreductases are employed.

6. The food product of claim 1 which is cheese.

* * * * *

UNITED STATES PATENT AND TRADEMARK OFFICE
CERTIFICATE OF CORRECTION

PATENT NO. : 5,747,078
DATED : May 5, 1998
INVENTOR(S) : Sylvia Josefine DE JONG; Ben Rudolf DE HAAN; and Hong Sheng TAN It is certified that error appears in the above-identified patent and that said Letters Patent is hereby corrected as shown below:

In the Abstract:

Line 6, change "form" to -- from --.

Signed and Sealed this

Eighth Day of September, 1998

Attest:

BRUCE LEHMAN

*Attesting Officer*     Commissioner of Patents and Trademarks